United States Patent
Ito et al.

(10) Patent No.: US 7,704,672 B2
(45) Date of Patent: Apr. 27, 2010

(54) PHOTOSENSITIVE SILANE COUPLING AGENT, METHOD OF MODIFYING SURFACE, METHOD OF FORMING PATTERN, AND METHOD OF FABRICATING DEVICE

(75) Inventors: Toshiki Ito, Kawasaki (JP); Natsuhiko Mizutani, Tokyo (JP); Takako Yamaguchi, Kawasaki (JP); Yasuhisa Inao, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 594 days.

(21) Appl. No.: 11/705,787

(22) Filed: Feb. 14, 2007

(65) Prior Publication Data
US 2007/0218398 A1    Sep. 20, 2007

(30) Foreign Application Priority Data
Mar. 14, 2006   (JP)   ............................. 2006-070001

(51) Int. Cl.
*G03F 7/00*   (2006.01)
*G03F 7/004*   (2006.01)
(52) U.S. Cl. .................................... 430/270.1; 430/331
(58) Field of Classification Search .............. 430/270.1, 430/312, 331
See application file for complete search history.

(56) References Cited

U.S. PATENT DOCUMENTS

| | | | | |
|---|---|---|---|---|
| 5,378,502 A * | 1/1995 | Willard et al. .............. | 427/305 |
| 5,648,201 A * | 7/1997 | Dulcey et al. ................ | 430/324 |
| 5,692,003 A | 11/1997 | Wingreen et al. .............. | 372/50 |
| 5,747,503 A * | 5/1998 | Rothman et al. ............. | 514/294 |
| 6,436,615 B1 * | 8/2002 | Brandow et al. ............. | 430/324 |
| 6,755,953 B2 | 6/2004 | Baba ........................... | 205/74 |
| 7,022,463 B2 | 4/2006 | Yamaguchi et al. .......... | 430/291 |
| 7,079,250 B2 | 7/2006 | Mukai ......................... | 356/445 |
| 7,204,915 B2 | 4/2007 | Kitade et al. .............. | 204/192.2 |
| 7,220,482 B2 | 5/2007 | Mino et al. .................. | 428/403 |
| 7,309,658 B2 * | 12/2007 | Lazovsky et al. ............ | 438/754 |
| 7,405,034 B2 * | 7/2008 | Yan et al. .................... | 430/312 |
| 2003/0129654 A1 * | 7/2003 | Ravkin et al. ................ | 435/7.1 |
| 2004/0223142 A1 | 11/2004 | Inao et al. ................. | 356/237.1 |
| 2007/0141483 A1 | 6/2007 | Yamaguchi et al. ............ | 430/5 |
| 2007/0212806 A1 | 9/2007 | Ito ................................ | 438/99 |
| 2007/0218373 A1 | 9/2007 | Ito et al. ........................ | 430/5 |

FOREIGN PATENT DOCUMENTS

DE   3841571 A *   6/1989

(Continued)

OTHER PUBLICATIONS

English abstract of JP 01-161336A (no date).*

(Continued)

*Primary Examiner*—Amanda C. Walke
(74) *Attorney, Agent, or Firm*—Fitzpatrick, Cella, Harper & Scinto

(57) ABSTRACT

Provided are a photosensitive silane coupling agent for forming a low-defect microparticle pattern, dot array pattern, or hole array pattern through fewer steps, and a method of forming a pattern using such photosensitive silane coupling agent. Used is a photosensitive silane coupling agent comprising a 1,2-naphthoquinone-2-diazido-5-sulfonyl group or a 1,2-naphthoquinone-2-diazido-4-sulfonyl group.

7 Claims, 5 Drawing Sheets

FOREIGN PATENT DOCUMENTS

| | | | |
|---|---|---|---|
| JP | 01161336 A | * | 6/1989 |
| JP | 06202343 A | * | 7/1994 |
| JP | 10-12968 | | 1/1998 |
| JP | 11-218627 | | 8/1999 |
| JP | 2001-168317 | | 6/2001 |
| JP | 2003-168606 | | 6/2003 |
| JP | 2003-268592 | | 9/2003 |
| JP | 2005-190624 | | 7/2005 |
| JP | 2007240981 A | * | 9/2007 |

OTHER PUBLICATIONS

Takashi Tamura, et al., "Synthesis of mesoporous thin film containing 2-nitrobenzyl group and introduction of carboxy groups patterned on the surface by photoirradiation", Polymer Preprints, Japan, vol. 53, No. 2, 2004, p. 4196.

Takashi Tamura, et al., "Synthesis of mesoporous thin film containing 2-nitrobenzyl group and introduction of carboxy groups patterned on the surface by photoirradiation", Polymer Preprints, Japan, vol. 53, No. 2, 2004, p. 4196. (with translation).

* cited by examiner

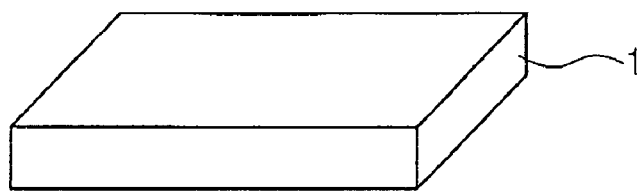
FIG. 1A
↓ FORMATION OF A SILANE COUPLING AGENT LAYER
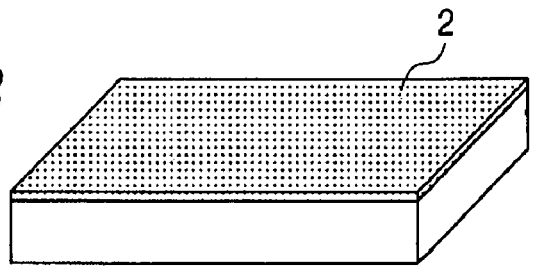
FIG. 1B
↓ EXPOSURE TO A PATTERN SHAPE
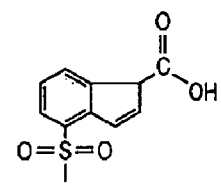
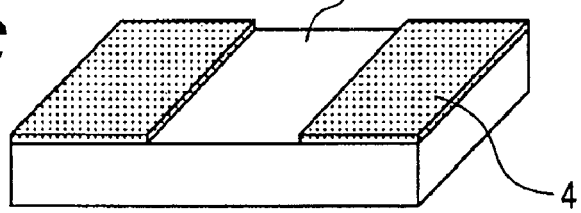
FIG. 1C
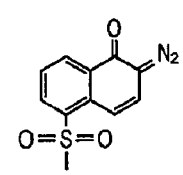
↓ DIPPING IN A COLLOIDAL SOLUTION
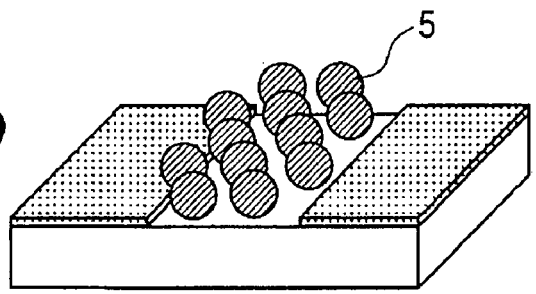
FIG. 1D

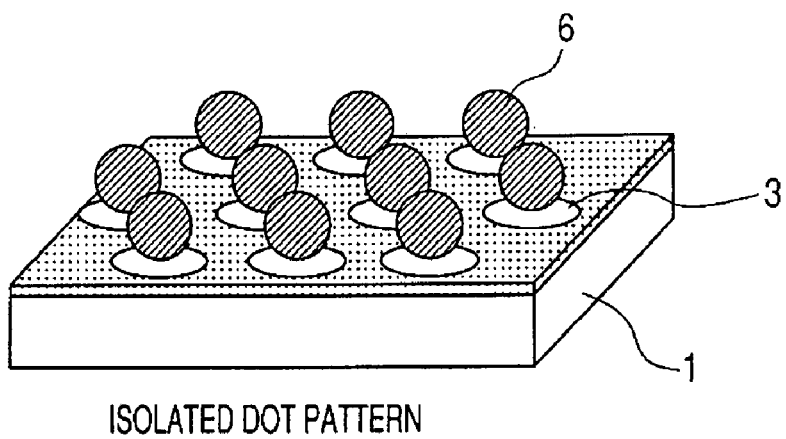
FIG. 2A  ISOLATED DOT PATTERN
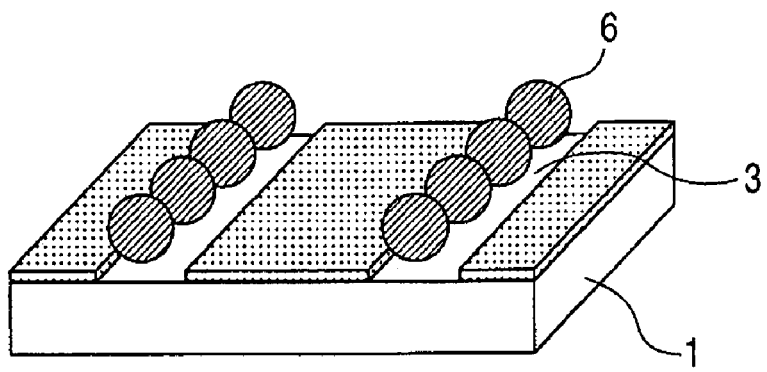
FIG. 2B  ISOLATED LINE PATTERN
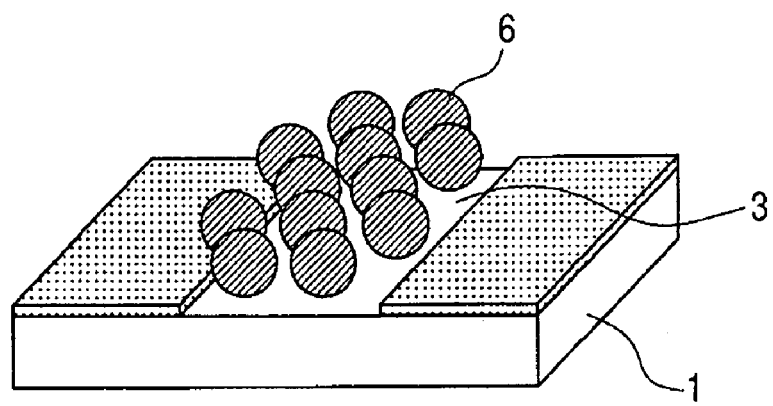
FIG. 2C  CLOSEST PACKED PATTERN
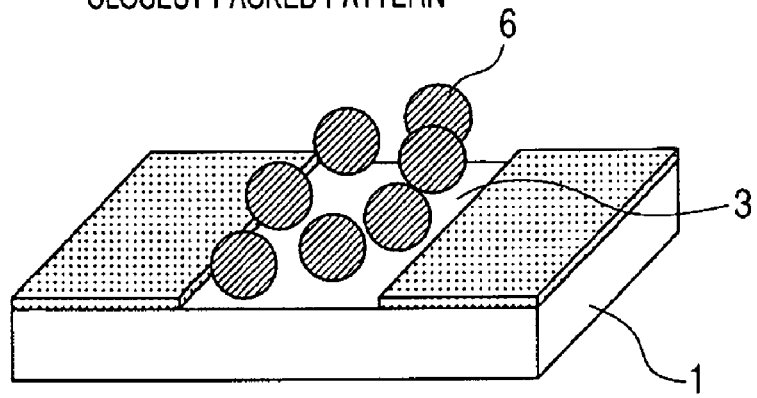
FIG. 2D  RANDOM PATTERN

FILM FORMATION

LIFT OFF

PHOTOSENSITIVE SILANE COUPLING AGENT, METHOD OF MODIFYING SURFACE, METHOD OF FORMING PATTERN, AND METHOD OF FABRICATING DEVICE

BACKGROUND OF THE INVENTION

1. Field of the Invention

The present invention relates to a photosensitive silane-coupling agent, a method of modifying a surface and a method of forming a pattern using such photosensitive silane coupling agent, and a method of fabricating a device.

2. Description of the Related Art

Recently, in the fields of various electronic devices which require microfabrication, such as semiconductor devices, there has been ever increasing demands for increased density and integration of the devices. In the step of fabricating a semiconductor device, it is the photolithography process that plays an important part in forming the fine circuit pattern.

Most current photolithography processes are carried out by reduced projection exposure. However, the resolution of reduced projection exposure is limited by the light diffraction limit, which is about one-third the wavelength of the light source. Thus, attempts have been made to achieve shorter wavelengths using techniques such as employing an excimer laser as the exposure light source, whereby microfabrication at about the 100 nm level is now possible.

Thus, although photolithography continues to have improving fineness, many problems needing to be resolved have arisen, such as the increased size of the equipment resulting from shortening the wavelength of the light source, as well as development of lenses for such wavelength region, equipment costs and costs of the corresponding lenses.

Further, devices have recently been proposed which require a high-density dot array pattern. Examples thereof include a single-electron device (Japanese Patent Application Laid-Open No. 2001-168317), patterned media (Japanese Patent Application Laid-Open No. 2005-190624), a chemical sensor (Japanese Patent Application Laid-Open No. 2003-268592), a quantum dot laser element (Japanese Patent Application Laid-Open No. H10-012968), and a photonic crystal optical device (Japanese Patent Application Laid-Open No. H11-218627). However, because these devices require even greater high-precision microfabrication techniques than those for semiconductor devices, mass production has been difficult with conventional photolithography techniques.

On the other hand, as a low-cost and simple method for forming a micropattern taking the place of lithography techniques, methods have been reported which cause the microparticles to arrange in a self-organizing manner.

Further, in recent years methods have also been proposed for forming a micropattern by forming a chemically reactive group in a pattern on a substrate surface using an energy beam, and then utilizing the interaction between the chemically reactive group and the microparticles. Specific examples are disclosed in Polymer Preprints, Japan, Japanese Ed., Vol. 53, 4196 (2004) and Japanese Patent Application Laid-Open No. 2003-168606. These examples are techniques which fuse lithography and self-organization. In the present invention such techniques will be referred to as "build-up lithography".

In Polymer Preprints, Japan, Japanese Ed., Vol. 53, 4196 (2004), it is disclosed to expose a monomolecular film of a photosensitive silane coupling agent to a light, and then adhere microparticles to the exposed portion.

Specifically, it is disclosed to irradiate UV rays onto a photosensitive silane coupling agent having a carboxyl group which is protected by a nitrobenzyl group to thereby generate a carboxyl group on the irradiated portion, and to dip the resultant object in an aqueous solution of fluorescent microparticles for selectively adhering fluorescent microparticles to the exposed portion.

Polymer Preprints, Japan, Japanese Ed., Vol. 53, 4196 (2004) also discloses the results of examples in which a monomolecular film of a photosensitive silane coupling agent having an unsaturated alkyl group was irradiated with X-rays in a pattern to excite the unsaturated bonds of the exposed portion, whereby bonds were formed with the organic film of the surface of the metal microparticles.

The photosensitive silane coupling agent used in Polymer Preprints, Japan, Japanese Ed., Vol. 53, 4196 (2004), which has a carboxyl group protected by a nitrobenzyl group, generates a nitrosobenzaldehyde as a byproduct upon exposure. To remove this byproduct, a rinsing step is necessary. However, in mass production of a device, a smaller number of steps is preferable from the perspective of costs.

Further, in Japanese Patent Application Laid-Open No. 2003-168606, there is the problem of a high rate of defects due to the microparticles not properly adhering to the energy beam irradiation portion. This is because the excited state of the unsaturated bond group is easily deactivated to the ground state.

SUMMARY OF THE INVENTION

The photosensitive silane coupling agent according to the present invention comprises a 1,2-naphthoquinone-2-diazido-5-sulfonyl group or a 1,2-naphthoquinone-2-diazido-4-sulfonyl group.

The above-described photosensitive silane coupling agent preferably has a structure represented by the following general formula (1),

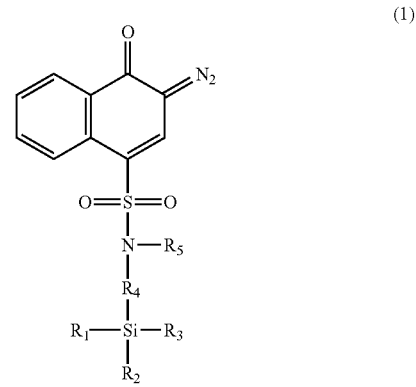

wherein at least one of $R_1$, $R_2$ and $R_3$ is an alkoxy group or a halogen atom, the other(s) being selected from the group consisting of an alkyl group, an alkenyl group and a hydrogen atom; $R_4$ is an alkylene group part of hydrogen atoms of which may be substituted with a fluorine atom or an alkyl group, a phenylene group part of hydrogen atoms of which may be substituted with a fluorine atom or an alkyl group, a naphthylene group part of hydrogen atoms of which may be substituted with a fluorine atom or an alkyl group, or a divalent group having a structure in which at least two of these divalent groups are bonded to each other; and $R_5$ is a hydrogen atom or an alkyl group.

The above-described photosensitive silane coupling agent preferably has a structure represented by the following general formula (2),

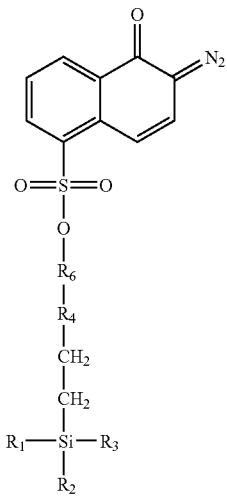

(2)

wherein $R_1$ to $R_4$ are defined in the same manner as in formula (1).; and $R_6$ is a methylene or alkylene group, part of hydrogen atoms of which may be substituted with a fluorine atom or an alkyl group.

The above-described photosensitive silane coupling agent preferably has a structure represented by the following general formula (3),

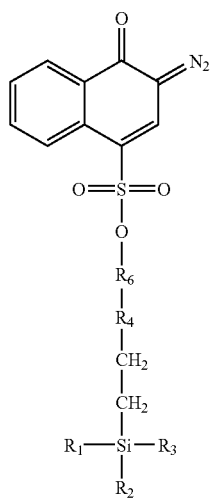

(3)

wherein $R_1$ to $R_4$ are defined in the same manner as in formula (1); and $R_6$ is defined in the same manner as in formula (2).

The above-described photosensitive silane coupling agent preferably has a structure represented by the following general formula (4),

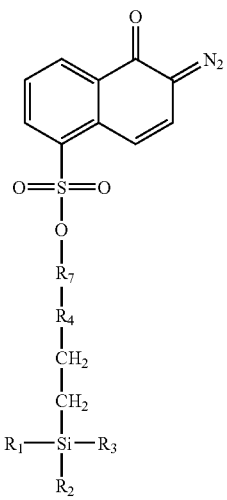

(4)

wherein $R_1$ to $R_4$ are defined in the same manner as in formula (1); and $R_7$ is a phenylene group part of hydrogen atoms of which may be substituted with a fluorine atom or an alkyl group, or a naphthylene group part of hydrogen atoms of which may be substituted with a fluorine atom or an alkyl group.

The above-described photosensitive silane coupling agent preferably has a structure represented by the following general formula (5),

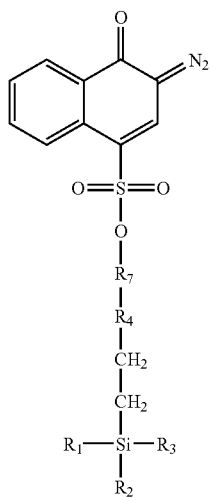

(5)

wherein $R_1$ to $R_4$ are defined in the same manner as in formula (1); and $R_7$ is defined in the same manner as in formula (4).

The present invention also encompasses a method of modifying a surface. The method of modifying a surface according to the present invention comprises the steps of layering the above-described photosensitive silane coupling agent onto a surface of a support, and generating a carboxyl group on the photosensitive silane coupling agent by radiation exposure.

The method of forming a microparticle pattern according to the present invention forms a pattern having a structure wherein a plurality of microparticles with an average particle diameter of at least 0.5 nm and at most 500 nm are arranged on a substrate, the method comprising the steps of layering the above-described photosensitive silane coupling agent onto a surface of a substrate, exposing the photosensitive silane coupling agent patternwise, generating a carboxyl group on the photosensitive silane coupling agent in an exposed portion, and selectively arranging microparticles on the exposed portion or unexposed portion.

The present invention also encompasses a method of fabricating a device. The method of fabricating a device according to the present invention fabricates a device using the method of forming a pattern according to the present invention.

Further features of the present invention will become apparent from the following description of exemplary embodiments with reference to the attached drawings.

BRIEF DESCRIPTION OF THE DRAWINGS

FIGS. 1A, 1B, 1C and 1D are a process chart illustrating one embodiment of a method for forming a microparticle pattern using the photosensitive silane coupling agent according to the present invention.

FIGS. 2A, 2B, 2C and 2D are a schematic diagram illustrating a microparticle pattern formed by selectively arranging microparticles (A) only on an exposed portion or an unexposed portion.

DESCRIPTION OF THE EMBODIMENTS

Figure 3:
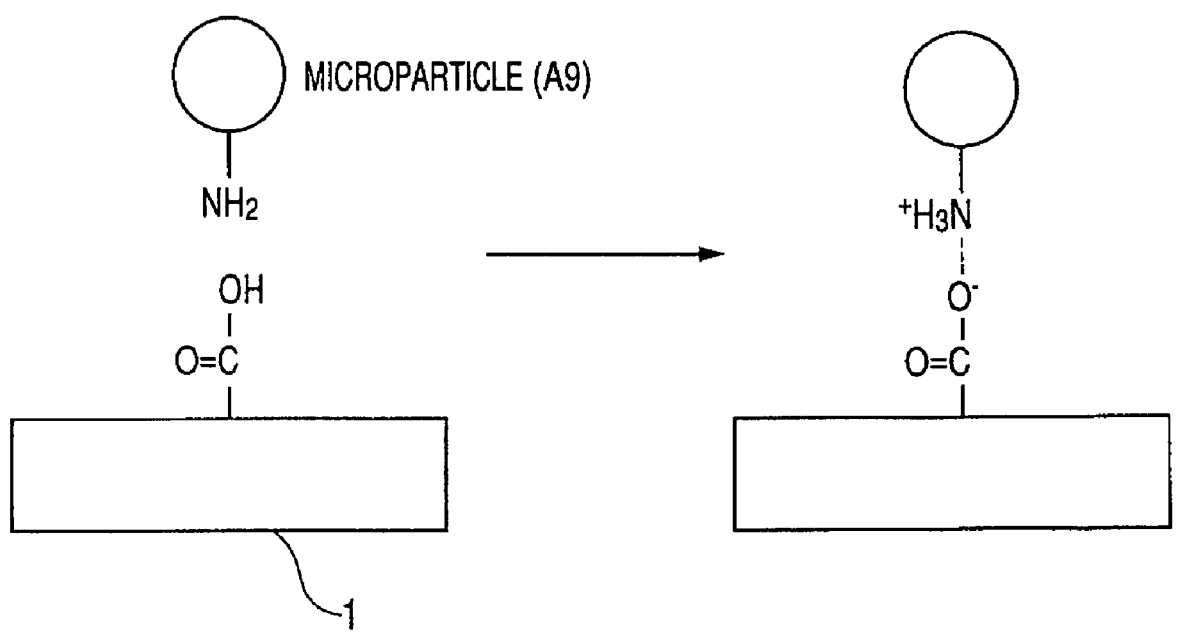
FIG. 3 is an explanatory diagram illustrating the bond between a carboxyl group on the exposed substrate portion and an amino group on the surface end of a microparticle.

The present invention will now be described in more detail.

The photosensitive silane coupling agent according to the present invention comprises a 1,2-naphthoquinone-2-diazido-5-sulfonyl group ("5-DNQ group") or a 1,2-naphthoquinone-2-diazido-4-sulfonyl group ("4-DNQ group").

The 5-DNQ group or 4-DNQ group is hydrophobic prior to exposure. However, as illustrated by the following chemical formula, the group shifts as a result of exposure, whereby an indene carboxyl group is generated, thereby causing the group to become hydrophilic. The only byproduct formed from the photoreaction is nitrogen.

The fact that the 5-DNQ group and 4-DNQ group have a substantial contrast between pre- and post-exposure hydrophobic and hydrophilic properties can be demonstrated using a so-called DNQ-novolac resist; that is, a resist constituted from a DNQ-group-containing compound and a cresol novolac resin. This is described in, for example, Kankosei Kobunshi ("Photosensitive Polymers"), Gentaro NAGAMATSU and Hideo INUI, published by Kodansha Scientific Ltd., 1977.

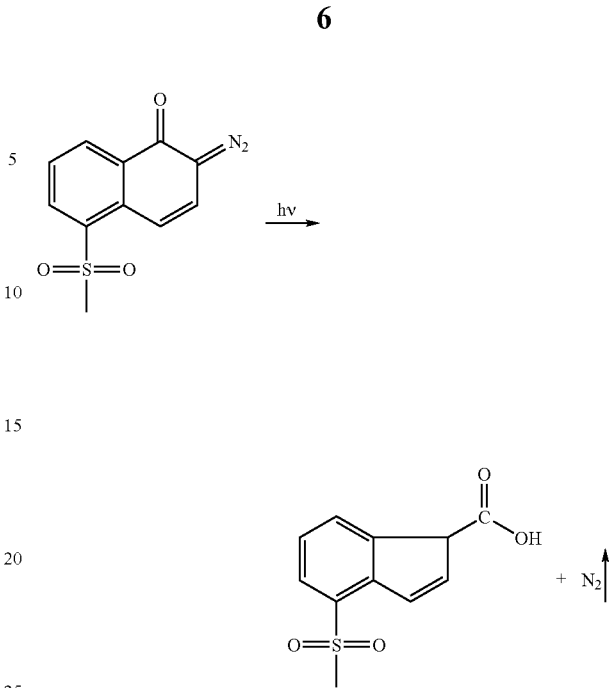

The method of synthesizing the photosensitive silane coupling agent according to the present invention will now be described in detail.

The, photosensitive silane coupling agent (1) can be obtained by reacting at room temperature 1,2-naphthoquinone-2-diazido-4-sulfonyl chloride and a silane coupling agent containing a primary or secondary amino group in the presence of a tertiary amine. The tertiary amine may be triethylamine, dimethylaminopyridine or the like. The 1,2-naphthoquinone-2-diazido-4-sulfonyl chloride, triethylamine and dimethylaminopyridine are all commercially available.

Specific examples of the silane coupling agent containing a primary or secondary amino group include, but are not limited to, products which are commercially available, such as aminophenyltrimethoxysilane, 3-aminopropyldimethylethoxysilane, 3-aminopropylmethyl-diethoxysilane, 3-aminopropyltriethoxysilane, 3-amino-propyltrimethoxysilane, N-methylaminopropyltrimethoxysilane, N-methylaminopropylmethyldimethoxysilane and N-ethylaminoisobutyltrimethoxysilane.

As illustrated by the following reaction formula, the above-described photosensitive silane coupling agent (2) can be obtained by reacting compound (10) with compound (11) with chloroplatinic (IV) acid hexahydrate ($H_2PtCl_6 \cdot H_2O$) as a catalyst. Compound (10) can be obtained by reacting at room temperature 1,2-naphthoquinone-2-diazido-5-sulfonyl chloride (7) and compound (9) in the presence of a tertiary amine such as triethylamine or dimethylaminopyridine.

Specific examples of compound (9) include, but are not limited to, products which are commercially available, such as allyl alcohol, 2-butenol, 4-pentenol, 10-undecenol and the like. Specific examples of compound (11) include, but are not limited to, products which are commercially available, such as trimethoxysilane, triethoxysilane, methyldiethoxysilane, dimethylethoxysilane, trichlorosilane, dichloromethylsilane, chlorodimethylsilane and the like.

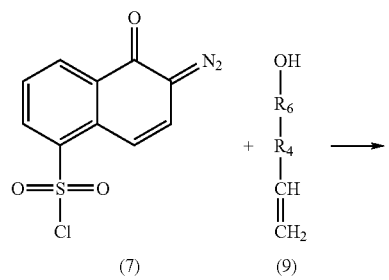

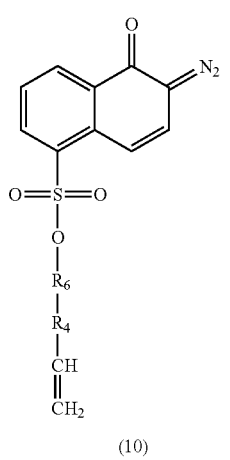

In the formula, $R_4$ is defined in the same manner as in formula (1) and $R_6$ is defined in the same manner as in formula (2).

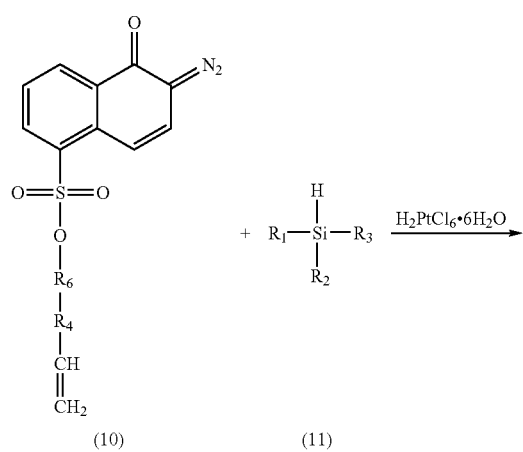

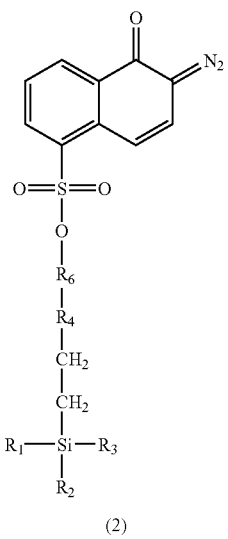

In the formula, $R_1$ to $R_4$ are defined in the same manner as in formula (1) and $R_6$ is defined in the same manner as in formula (2).

In addition, the above-described photosensitive silane coupling agent (3) can be synthesized in the same manner as the photosensitive silane coupling agent (2) by using 1,2-naphthoquinone-2-diazido-4-sulfonyl chloride in place of the 1,2-naphthoquinone-2-diazido-5-sulfonyl chloride (7).

The above-described photosensitive silane coupling agent (4) can be obtained by reacting compound (13) with compound (11) with chloroplatinic (IV) acid hexahydrate ($H_2PtCl_6 \cdot H_2O$) as a catalyst. Compound (13) can be obtained by reacting at room temperature 1,2-naphthoquinone-2-diazido-5-sulfonyl chloride (7) and compound (12) in the presence of a tertiary amine such as triethylamine or dimethylaminopyridine. Specific examples of compound (12) include products which are commercially available, such as 4-vinylphenol, 2-allylphenol, 4-allyl-2,6-dimethoxyphenol, 3-allyl-4-hydroxyacetophenol, 2-ethoxy-5-(1-propenyl)phenol and the like. However, compound (12) is not limited to these examples.

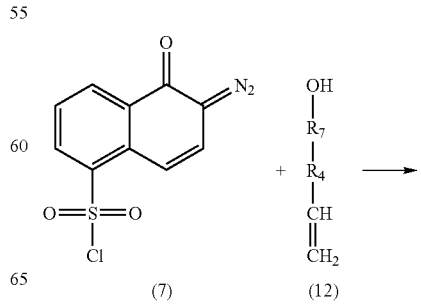

-continued

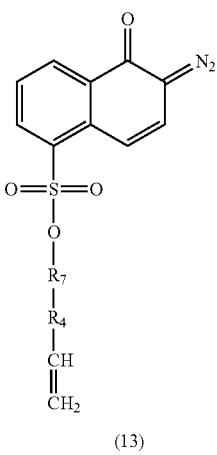

(13)

In the formula, $R_4$ is defined in the same manner as in formula (1) and $R_7$ is defined in the same manner as in formula (4).

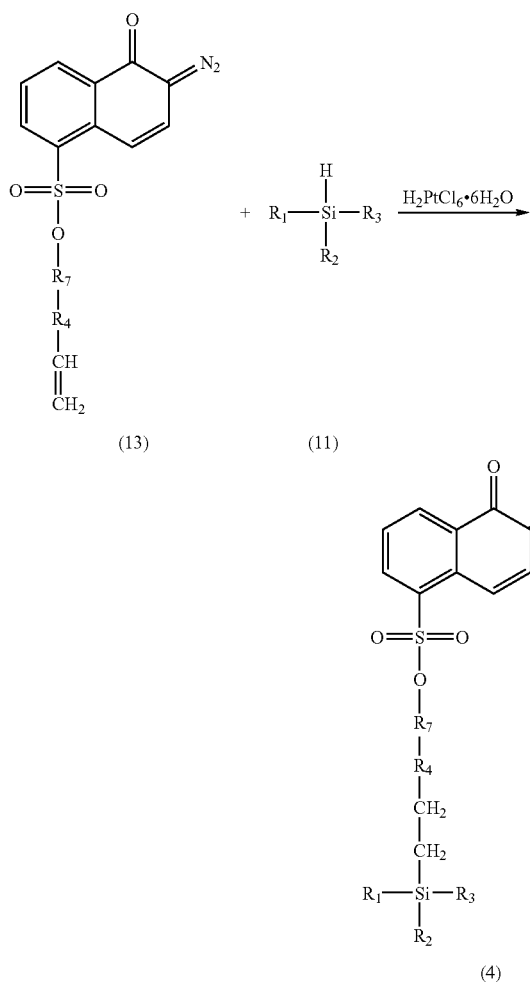

In the formula, $R_1$ to $R_4$ are defined in the same manner as in formula (1) and $R_7$ is defined in the same manner as in formula (4).

In addition, the above-described photosensitive silane coupling agent (5) can be synthesized in the same manner as the photosensitive silane coupling agent (4) by using 1,2-naphthoquinone-2-diazido-4-sulfonyl chloride in place of the 1,2-naphthoquinone-2-diazido-5-sulfonyl chloride (7).

A method of modifying a surface using the above-described photosensitive silane coupling agent will now be described in more detail. The photosensitive silane coupling agent according to the present invention is immobilized on a support surface via a chemical bond. Examples of a suitable support include a substrate or the microparticles (B).

Examples of the substrate include a metal substrate, a semiconductor substrate., an insulating substrate such as glass, quartz, BN or the like, and a substrate having one or plural kinds of resist, spin-on-glass, metal, oxide, nitride or the like formed as a film on such substrates. A wide variety of such substrates can be subjected to surface modification. The substrate preferably has hydroxyl groups formed on the surface.

To form a hydroxyl group on the substrate surface, it is preferable to perform pretreatment of the substrate as necessary. The pre-treatment can be carried out by exposing the substrate surface to an acidic solution or a UV ray-ozone atmosphere. Examples of the acidic solution include sulfuric acid, hydrochloric acid, nitric acid, hydrogen peroxide and the like. These may be used alone or in combination of two or more thereof. A combination of sulfuric acid and hydrogen peroxide is preferable. For pre-treatment of a silicon substrate, the combination of sulfuric acid and hydrogen peroxide is especially preferable. Means for performing the pre-treatment with an acidic solution include coating, spraying, dipping and the like.

Examples of the microparticles (B) include quartz microparticles, metal oxide microparticles of alumina, gallium-oxide or the like, and gold microparticles. Such microparticles may be subjected to surface modification.

The photosensitive silane coupling agent according to the present invention may be coated onto the surface of the above-mentioned substrates and microparticles (B), which can then be heated to form a, photosensitive silane coupling agent layer. Coating of the photosensitive silane coupling agent can be carried out using a solution of just the photosensitive silane coupling agent or a solution in which the photosensitive silane coupling agent is dissolved in an organic solvent, by dipping, spin coating, spray coating, vapor deposition or the like. In the present invention, dipping is preferable.

After coating the photosensitive silane coupling agent, it is preferable to appropriately heat so as to complete the reaction with the hydroxyl groups on the substrate. Heating can be conducted using heating means such as a hotplate, a hot-air drier or the like, at a temperature of 80 to 200° C., and more preferably 80 to 150° C. As a result of the above-described treatment, a monomolecular layer of the photosensitive silane coupling agent according to the present invention is formed on the surface of the substrates or microparticles.

The photosensitive silane coupling agent layer according to the present invention formed in the above manner on a substrate or microparticle surface is, usually, exposed using a known exposure apparatus. As a result of exposure, a carboxyl group, is generated on the exposed portion.

The radiation rays used for exposure can be appropriately selected from among visible light, UV rays, far ultraviolet rays, X-rays, electron beam, γ rays, molecular beam, ion beam and the like. Especially preferred examples include the following: mercury lamp rays (wavelength of 436 nm, 365 nm and 254 nm); a KrF excimer laser beam (wavelength of 248 nm); an ArF excimer laser beam (wavelength of 193 nm); an F$_2$ excimer laser beam (wavelength of 157 nm); far UV rays such as extreme UV rays (EUV, wavelength of 13 nm), an electron beam and the like.

These radiation rays can be employed singly or in a plurality together.

Since the only byproduct formed from the photoreaction is nitrogen, there is no need for a rinsing step such as that required in Polymer Preprints, Japan, Japanese Ed., Vol. 53, 4196 (2004) for removing byproducts.

The method of forming a microparticle pattern according to the present invention is a method of forming a pattern having a structure wherein a plurality of microparticles with an average particle diameter of at least 0.5 nm and at most 500 nm are arranged on a substrate, the method comprising the steps of layering the photosensitive silane coupling agent according to the present invention onto a surface of a substrate, exposing the photosensitive silane coupling agent layer patternwise, generating a carboxyl group on the photosensitive silane coupling agent on an exposed portion, and selectively arranging microparticles on the exposed portion or unexposed portion.

The present invention also encompasses the method of forming a microparticle pattern further comprising the step of processing the substrate by etching with the microparticle pattern as a mask.

The present invention also encompasses the method further comprising the steps of forming a film over the entire substrate on which the microparticle pattern is formed, and forming a film pattern by removing the microparticle pattern and the film formed thereon.

In the present invention, the microparticles can be arranged using a colloidal solution containing the microparticles.

In the present invention, the exposure can be carried out using near-field light generated from an exposure mask which is provided with a light-shielding layer comprising an opening narrower than the wavelength of the exposure light source.

In the present invention, the microparticles may be formed of a material selected from the group consisting of metals, metal oxides, semiconductors and resins. Gold or gold nanorods can be used as the metal. In addition, magnetic microparticles, fluorescent microparticles, polystyrene microparticles and the like can also Abe employed.

The microparticles can also have an amino group on an end of the surface of the microparticles.

The present invention also encompasses a method of fabricating a device using the method of forming a microparticle pattern according to the present invention.

While various devices can be mentioned as examples of devices that can be fabricated, devices having a high-density dot pattern are preferred in terms of harnessing the present invention.

Specifically, a single-electron device can be fabricated by forming minute tunnel junction sites using the method of forming a microparticle pattern according to the present invention.

In addition, patterned media can be fabricated by forming a magnetic bit array using the method of forming a microparticle pattern according to the present invention.

Further, a chemical sensor can be fabricated by forming a metallic microparticle pattern using the method of forming a microparticle pattern according to the present invention.

In addition, a quantum dot laser element can be fabricated by forming a quantum dot array structure using the method of forming a microparticle pattern according to the present invention.

Further, a photonic crystal optical device can be fabricated by forming a two-dimensional photonic crystal structure using the method of forming a microparticle pattern according to the present invention.

According to the present invention, build-up lithography can be provided without requiring a rinsing step or a photolithography step that utilizes a resist.

Further provided are a photosensitive silane coupling agent which can form a low-defect pattern, and a method of modifying a surface and a method of forming a pattern using such photosensitive silane coupling agent.

EXAMPLES

The method of forming a pattern using the above-described photosensitive silane coupling agent will now be described in more detail based on the drawings.

FIGS. 1A, 1B, 1C and 1D are a process chart illustrating one embodiment of a method for forming a pattern using the photosensitive silane coupling agent according to the present invention.

The photosensitive silane coupling agent according to the present invention is immobilized on a substrate via a chemical bond. Examples of the substrate include a metal substrate, a semiconductor substrate, an insulating substrate such as glass, quartz, BN or the like. In addition, the substrate can be selected depending on the desired device from among a broad range of substrates having, for example, one or plural kinds of resist, spin-on-glass, metal, oxide, nitride or the like formed as a film on the above-described substrates. Preferably, a hydroxyl group is formed on the surface immobilizing the photosensitive silane coupling agent.

To form a hydroxyl group on the substrate surface, it is preferable to perform pre-treatment of the substrate as necessary. The pre-treatment can be carried out by exposing the substrate surface to an acidic solution or a UV ray-ozone atmosphere. Examples of the acidic solution include sulfuric acid, hydrochloric acid, nitric acid, hydrogen peroxide and the like. These may be used alone or in combination of two or more thereof. A combination of sulfuric acid and hydrogen peroxide is preferable. For pre-treatment of a silicon substrate, the combination of sulfuric acid and hydrogen peroxide is especially preferable. Means for performing the pre-treatment with an acidic solution include coating, spraying, dipping and the like.

The photosensitive silane coupling agent according to the present invention is coated onto the substrate 1 shown in FIG. 1A, which is then heated to form a photosensitive silane coupling agent layer 2 (FIG. 1B).

Coating of the photosensitive silane coupling agent can be carried out using a solution of just the photosensitive silane coupling agent or a solution in which the photosensitive silane coupling agent is dissolved in an organic solvent, by dipping, spin coating, spray coating, vapor deposition or the like. In the present invention, dipping or spin coating are preferable. After coating the photosensitive silane coupling agent, it is preferable to appropriately heat so as to complete the reaction with the hydroxyl groups on the substrate. Heating can be conducted using heating means such as a hotplate, a hot-air drier or the like, at a temperature of 80 to -200° C., and more preferably 80 to 150° C. As a result of this treatment, a monomolecular layer of the photosensitive silane coupling agent according to the present invention is formed.

The thus formed photosensitive silane coupling agent layer 2 according to the present invention is then normally exposed patternwise using a known exposure apparatus (FIG. 1C).

Carboxyl groups are selectively generated on the exposed portion 3 from the exposure. In FIG. 4, numeral 4 denotes an unexposed portion.

The radiation rays used for exposure can be appropriately selected from among visible light, UV rays, far ultraviolet rays, X-rays, electron beam, γ rays, molecular beam, ion beam and the like. Especially preferable are mercury lamp rays. (wavelength of 436 nm, 365 nm and 254 nm), a KrF excimer laser beam (wavelength of 248 nm), an ArF excimer laser beam (wavelength of 193 nm), and a $F_2$ excimer laser beam (wavelength of 157 nm). In addition, far UV rays such as extreme UV rays (EUV, wavelength of 13 nm), or an electron beam are also preferable. These radiation rays can be employed singly or in a plurality together.

As another exposure method, it is also preferable to use near-field light generated from a photomask which is provided with a light-shielding layer comprising an opening narrower than the wavelength of the exposure light source. As the radiation rays used for near-field light exposure, the above-described radiation rays can be employed. These radiation rays can be employed singly or in a plurality together. The exposure by near-field light is conducted by closely adhering the photomask shielding layer to the article to undergo exposure.

To achieve an even finer pattern, short-wavelength ArF excimer laser light, $F_2$ excimer laser light, EUV, an electron beam or near-field light, which is not affected by the diffraction limit, are preferable. Of these, a near-field light exposure apparatus is low cost as it does not require an accurate optical system or expensive light source, and is thus especially preferable in the present invention in terms of productivity.

As a result of the exposure, the carboxyl groups immobilized on the substrate are generated patternwise on the exposed portion. The photochemical reaction of the photosensitive silane coupling agent according to the present invention is an irreversible reaction. Thus, there is no deactivation of the chemically reactive groups on the exposed portion, as in the above-described prior examples (Japanese Patent Application Laid-Open No. 2003-168606), which enables a microparticle pattern having few defects to be formed.

Since the only byproduct formed from the photoreaction is nitrogen, there is no need for a rinsing step such as that required in Polymer Preprints, Japan, Japanese Ed., Vol. 53, 4196 (2004) for removing byproducts.

After exposure has been completed, the substrate is dipped in a colloidal solution in which microparticles (A) 5 are dispersed. As a result of this step, if the surface is hydrophilic the microparticles (A) 5 selectively adhere to the exposed portion, while if the surface is hydrophobic the microparticles (A) 5 selectively adhere to the unexposed portion (FIG. 1D).

As illustrated in FIG. 3, if microparticles (A9) having an amino group on their surface end are used as the microparticles (A), the amino groups and the carboxyl groups on the substrate 1 are linked by ionic bonds.

FIGS. 2A, 2B, 2C and 2D are a schematic diagram illustrating a microparticle pattern formed by selectively arranging microparticles (A) 6 only on an exposed portion or an unexposed portion. The shape of the pattern may be an isolated dot pattern (FIG. 2A), wherein one microparticle 6 is adhered per one location of microdot-shaped exposed portion 3 or unexposed portion on the substrate 1; or an isolated line pattern (FIG. 2B), wherein the microparticles 6 are aligned in one line in a narrow line pattern. The shape of the pattern may also be a closest packed pattern. (FIG. 2C), wherein the microparticles 6 are arranged in a closest packed manner on the exposed portion 3 or unexposed portion which are broader than the size of the microparticles. The shape of the pattern may also be a random pattern. (FIG. 2D), wherein the, microparticles are randomly arranged on the exposed portion 3 or unexposed portion which are broader than the size of the microparticles, with a certain interval between the microparticles as a result of the repulsive force therebetween. These patterns may be freely formed depending on the intended device. In addition, the patterns which are formed are not limited to those described above.

Various devices can be fabricated using the microparticle pattern formed in the above-described manner.

The kind of microparticles (A) may be selected depending on the intended device. If it is intended to fabricate a single-electron device, microparticles can be used which are conductive, such as those consisting of a metal or a metal oxide.

If it is intended to fabricate a magnetic recording medium, such as patterned media, the following materials 3 can be used. Specific examples include magnetic metal microparticles (A6) selected from the group consisting of Co, Ni, Fe, FePt, CoPt, CoNi, CoCr, CoP, CoNiP, FeCoB, FeCoNi, CoNiFeB, FeNi, FeCo, CoNiPt and the like.

If it is intended to fabricate a chemical sensor, metal microparticles (A1) can be used. From the perspectives of sensitivity and chemical stability, noble metals are preferred, and gold microparticles (A4) or gold nanorods (A5) are especially preferred.

If it is intended to fabricate a quantum dot laser element, semiconductor microparticles (A3), such as Si, SiGe, GaAs, InGaAs, GaN, InP, InAs, AlGaAs, InGaAsP, GaInAlP, InGaN, AlGaN and the like can be used.

Figure 4A:
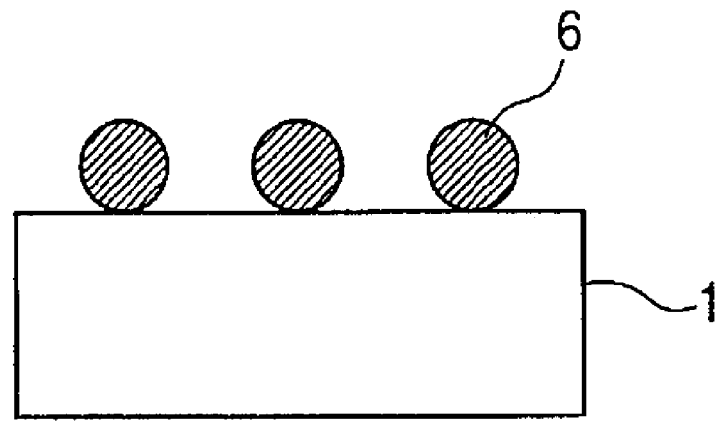
FIGS. 4A and 4B are an explanatory, diagram illustrating a dry etching process with microparticles as a mask.
Figure 4B:
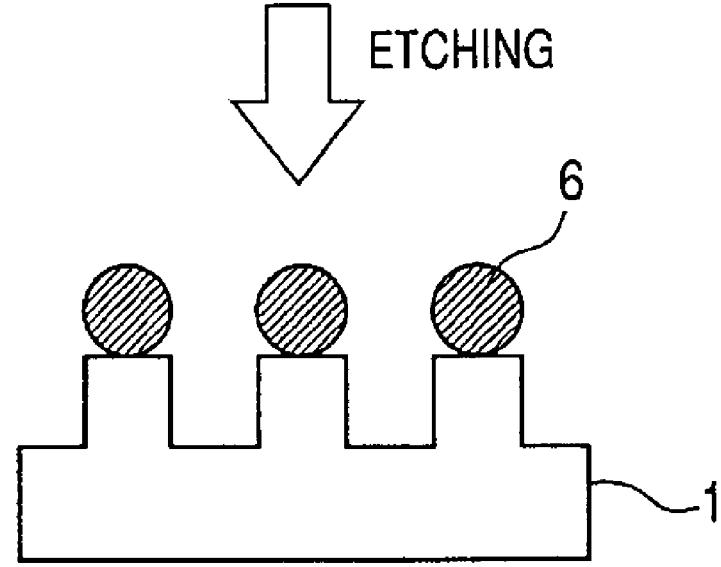

FIGS. 4A and 4B are an explanatory diagram illustrating a dry etching process with microparticles as. a mask. As illustrated in FIGS. 4A and 4B, a dot array pattern may be formed by processing a substrate material with the microparticle pattern formed in the above-described manner as an etching mask by dry etching using reactive plasma or radicals, ion milling or wet etching. Reference numerals 1 and 6 denote a substrate and a microparticles, respectively.

The substrate material may be selected depending on the intended device. If it is intended to fabricate a single-electron device, a metal or a metal oxide may be used as the substrate material.

If it is intended to fabricate a magnetic recording medium, such as patterned media, the following magnetic materials may be used as the substrate material. Specific examples include Co, Ni, Fe, FePt, CoPt, CoNi, CoCr, CoP, CoNiP, FeCoB, FeCoNi, CoNiFeB, FeNi, FeCo, CoNiPt and the like.

If it is intended to fabricate a chemical sensor, from the perspectives of sensitivity and chemical stability, a noble metal is preferably used as the substrate material.

If it is intended to fabricate a quantum dot laser element, a semiconductor such as Si, SiGe, GaAs, InGaAs, GaN, InP, InAs, AlGaAs, InGaAsP, GaInAlP, InGaN, AlGaN and the like can be, used as the substrate material.

Processing of the substrate can be carried out by dry etching using reactive plasma or radicals, ion milling or wet etching. Dry etching using reactive plasma is especially preferable, as such process is suitable for forming a pattern which is fine and has high verticality.

The dry etching gas is selected depending on a substrate to be etched, and may be a plasma of a gas such as $CF_4$, $C_2F_6$, $C_3F_8$, $CCl_2F_2$, $CCl_4$, $CBrF_3$, $BCl_3$, $PCl_3$, $SF_6$, $Cl_2$, HCl, HBr, $O_2$, $N_2$, Ar or the like. The wet etching agent can be appropriately selected depending on a material to be etched. Examples of the wet etching agent include an aqueous solution of hydrofluoric acid, an aqueous solution of ammonium fluoride, an aqueous solution of phosphoric acid, an aqueous solution of acetic acid, an aqueous solution of nitric acid, an aqueous solution of ammonium cerium nitrate, an aqueous solution of potassium hydroxide, an aqueous solution of tetramethylammonium hydroxide and the like.

Figure 5A:
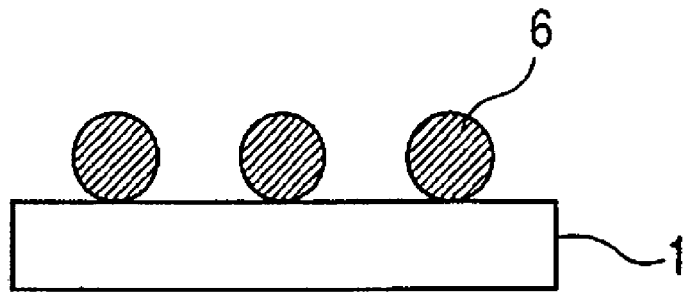
FIGS. 5A, 5B and 5C are an explanatory diagram illustrating a lifting-off process with microparticles as a mask.
Figure 5B:
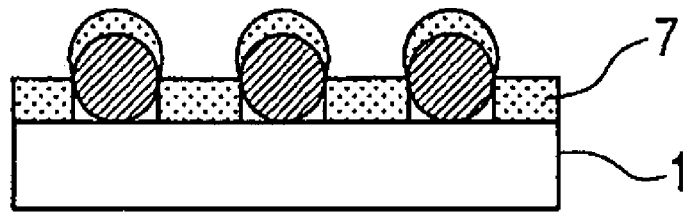
Figure 5C:
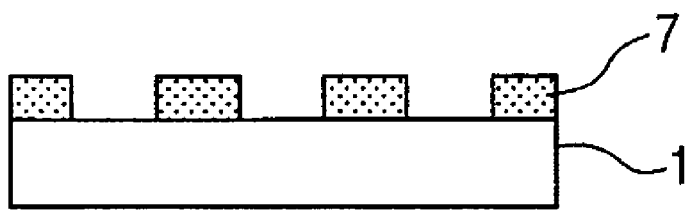

FIGS. 5A, 5B and 5C are an explanatory diagram illustrating a lifting-off process with microparticles as a mask. As illustrated in FIGS. 5A, 5B and 5C, a material layer 7 may be formed over the entire surface of the, substrate 1 having a microparticle 6 pattern formed as described above, to thereby form a hole array pattern of the desired material by lifting off.

Examples of the material layer forming method include various kinds of physical vapor deposition (PVD), and coating methods such as dipping, spin-coating and the like. Specific examples of PVD methods include various vacuum deposition methods such as electron beam heating, resistance heating, and flash evaporation, plasma deposition, various sputtering methods such as bipolar sputtering, DC sputtering, DC magnetron sputtering, high-frequency sputtering, magnetron sputtering, ion beam sputtering and bias sputtering, a DC method, an RF method, a multi-cathode method, an activated reaction method, electric field deposition, and various ion plating methods such as high-frequency ion plating and reactive ion plating.

After film formation, the microparticles and the film adhered thereon are removed by dipping into an organic solvent, an aqueous alkali solution, an aqueous acidic solution or the like. It is preferable to carry out heating, rocking and the like as necessary.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Laid-Open No. 2006-070001, filed Mar. 14, 2006, which is hereby incorporated by reference herein in its entirety.

What is claimed is:

1. A method of forming a microparticle pattern having a structure wherein a plurality of microparticles with an average particle diameter of at least 0.5 nm and at most 500 nm are arranged on a substrate, the method comprising the steps of:
   layering a photosensitive silane coupling agent comprising 1,2-naphthoquinone-2-diazido-5-sulfonyl group or, 2-naphthoquinone-2-diazido-4-sulfonyl group onto a surface of the substrate, exposing the photosensitive silane coupling agent layer patternwise, generating a carboxyl group on the photosensitive silane coupling agent in an exposed portion, and selectively arranging the microparticles on the exposed portion or unexposed portion,
   wherein the microparticles are arranged by using a colloidal solution comprising the microparticles.

2. A method of forming a microparticle pattern having a structure wherein a plurality of microparticles with an average particle diameter of at least 0.5 nm and at most 500 nm are arranged on a substrate, the method comprising the steps of:
   layering a photosensitive silane coupling agent comprising 1,2-naphthoquinone-2-diazido-5-sulfonyl group or, 2-naphthoquinone-2-diazido-4-sulfonyl group onto a surface of the substrate, exposing the photosensitive silane coupling agent layer patternwise, generating a carboxyl group on the photosensitive silane coupling agent in an exposed portion, and selectively arranging the microparticles on the exposed portion or unexposed portion,
   wherein the microparticles have an amino group on an end of the surface of the microparticles.

3. A method of fabricating a single-electron device by forming minute tunnel junction sites using said method of forming a microparticle pattern according to claim 2.

4. A method of fabricating a patterned medium by forming a magnetic bit away using said method of forming a microparticle pattern according to claim 2.

5. A method of fabricating a chemical sensor by forming a metallic microparticle pattern using said method of forming a microparticle pattern according to claim 2.

6. A method of fabricating a quantum dot laser element by forming a quantum dot away structure using said method of forming a microparticle pattern according to claim 2.

7. A method of fabricating a photonic crystal optical device by forming a two-dimensional photonic crystal structure using said method of forming a microparticle pattern according to claim 2.

* * * * *